United States Patent [19]

Kamami

[11] Patent Number: 5,611,796

[45] Date of Patent: Mar. 18, 1997

[54] HANDPIECE FOR A DEVICE FOR PERFORMING LASER SURGERY OF THE NOSE

[76] Inventor: Yves-Victor Kamami, 43, Boulevard Malesherbes, 75008 Paris, France

[21] Appl. No.: 510,967

[22] Filed: Aug. 3, 1995

[30] Foreign Application Priority Data

Aug. 4, 1994 [FR] France ................... 94 09704

[51] Int. Cl.$^6$ .................................................. A61B 17/36
[52] U.S. Cl. .................................................. 606/15
[58] Field of Search ................... 606/4, 5, 6, 14, 606/15, 16, 17

[56] References Cited

U.S. PATENT DOCUMENTS

| | | | |
|---|---|---|---|
| 3,865,113 | 2/1975 | Sharon et al. | 606/15 |
| 4,211,229 | 7/1980 | Wurster | 606/15 |
| 4,650,287 | 3/1987 | Kudo et al. | |
| 4,671,273 | 6/1987 | Lindsey | |
| 5,254,115 | 10/1993 | Bhatta et al. | 606/16 |
| 5,257,989 | 11/1993 | Celaya et al. | 606/16 |

FOREIGN PATENT DOCUMENTS 2438465  6/1979  France .

OTHER PUBLICATIONS

"CO$_2$ Laser Turbinectomies for Chronic Obstructive Rhinitis" (Mittelman); Lasers In Surgery and Medicine, No. 2, pp. 29–35 (1982).

Laser + Elektrooptik, vol. 10, No. 1 pp. 28–31 (1978).

Primary Examiner—Angela D. Sykes
Assistant Examiner—Sonya Harris-Ogugua
Attorney, Agent, or Firm—Michael, Best & Friedrich

[57] ABSTRACT

The invention relates to a handpiece for a device for performing laser surgery of the nose. It comprises a handle having a proximal end 36 including means enabling it to be connected to a source of laser radiation, a distal end 44 at which the laser radiation is supplied to a work zone, and a transit region 31, 52 for passing the laser radiation from the proximal end 36 to the distal end 44. According to the invention, the transit region 31 has a main axis 32 and the handpiece includes a distal region 4 forming an open channel 52 having an outside diameter 48 that it enables it to be inserted in the nostril of a patient, the device enabling high laser power to be delivered without giving rise to hemorrhage.

15 Claims, 1 Drawing Sheet

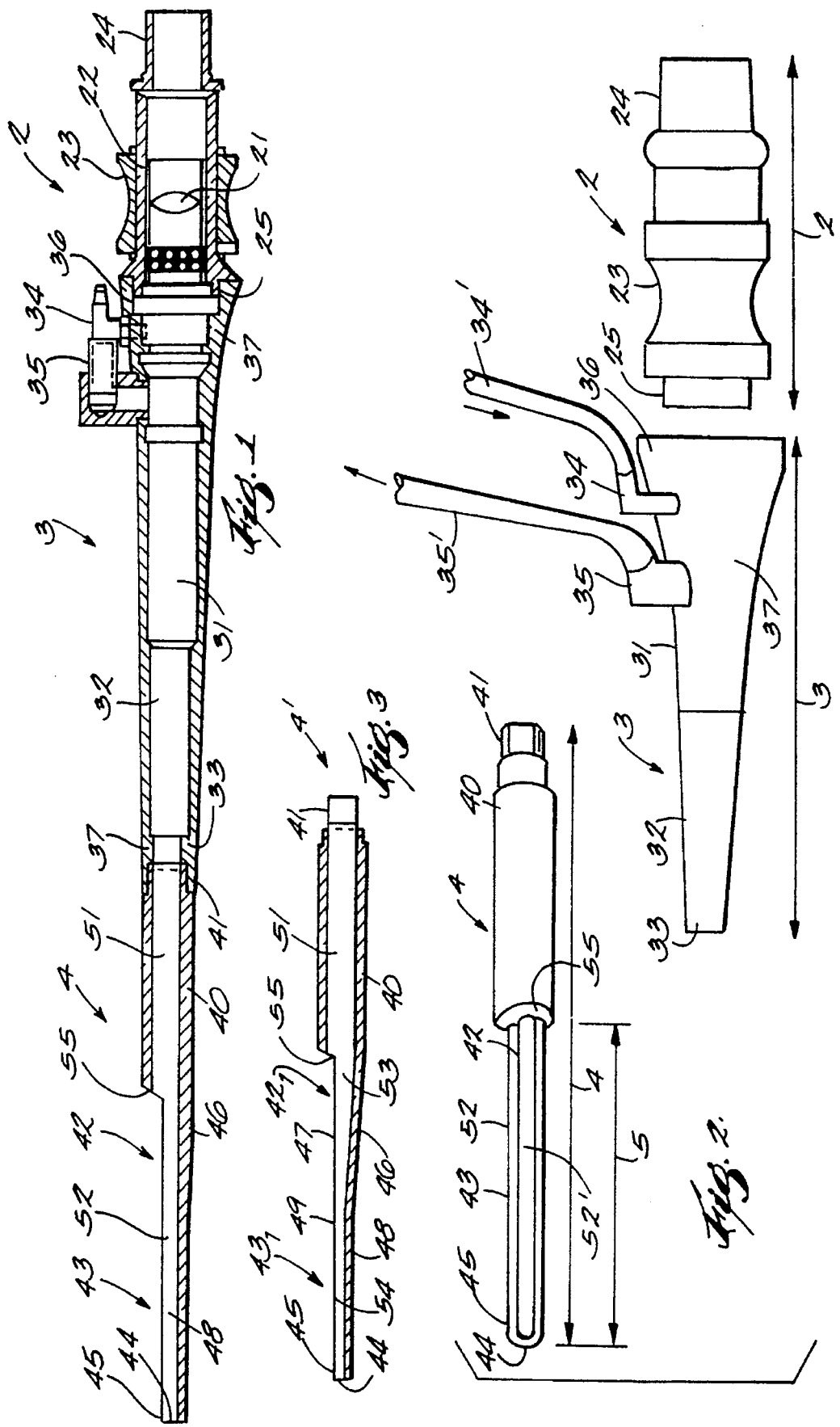

HANDPIECE FOR A DEVICE FOR PERFORMING LASER SURGERY OF THE NOSE

The present invention relates to a handpiece for a device for performing laser surgery of the nose.

BACKGROUND OF THE INVENTION

The treatment of hypertrophic chronic rhinitis (chronic blocked nose) generally requires major surgery in the form of turbinectomy under general anesthetic, and thus hospitalization, with the risks of hemorrhage and of postoperative pain.

For several years now, outpatient treatment has been available by means of laser surgery using nasal probes that include optical fibers curved to fit the shape of the nostril, and that make use either of a neodymium laser (Nd: YAG) which requires several visits repeated at intervals of several weeks because of the risks associated with using powers that are too high, or else of $CO_2$ lasers which are less risky since tissue absorption is more superficial, but which are difficult to use in this application because of technical obstacles. The laser radiation delivered by carbon dioxide lasers has a wavelength of 10.6 microns, and it is difficult to transmit power at that wavelength by means of optical fiber. In particular, one such optical fiber, e.g. that described in U.S. Pat. No. 4,930,863, issued Jun. 5, 1990 (Rauiot University—Tel Aviv), suffers from poor suitability for making nasal probes given that its diameter, which is of millimeter order, is too small, and above all because even when the working power of the laser is limited, the internal plastics material fiber that conveys the radiation and that is surrounded by a metal sheath can be used for little more than about ten times at best.

However, the article by Dr. Michael Sladkine, published on page 6 of the journal "Medical Laser Report" of June 1994 shows that following treatment performed by Dr. Joseph Krespi at Saint Luke's Hospital, New York, and by Dr. Yves-Victor Kamami (the inventor of the handpiece constituting the subject matter of the present patent application), the technique of performing surgery with a $CO_2$ laser is attractive, particularly because of short patient recovery time, making it possible to avoid the major drawbacks of pain and bleeding.

OBJECTS AND SUMMARY OF THE INVENTION

An object of the present invention is to provide a handpiece enabling nasal surgery to be performed by laser and considerably improving the effectiveness of the operation, and which can even enable nasal polyposis to be performed or hypertrophic chronic rhinitis to be operated in a single visit via the cavity of the nose.

Another object of the invention is to provide a handpiece for laser surgery of the nose which solves the above-mentioned wear problems, by avoiding the use of an optical fiber.

Finally, another object of the invention is to provide a handpiece for laser surgery of the nose, making it easy to use a $CO_2$ laser with maximum effectiveness.

To this end, the handpiece of the invention comprises a handle having a proximal end including means enabling it to be connected to a source of laser radiation, a distal end at which the laser radiation is delivered to a working zone, and a transit region though which the laser radiation passes from the proximal end to the distal end, wherein the transit region has a main axis, and wherein the handpiece includes a distal region forming an open channel and having an outside diameter enabling it to be inserted into the nostril of a patient.

The distal region is of a length sufficient to enable said distal end to reach at least the inferior nasal concha of a nose to be treated while simultaneously leaving a portion of the distal region forming the open channel outside the nose. This makes it easy for the practitioner to observe the ablation to be performed.

Advantageously, the distal region may include a first upstream portion that tapers progressively towards a first downstream portion which extends it and which is terminated by said distal end. The downstream portion can thus easily be inserted as far as the operating zone whereas the larger upstream portion can be used as a nostril spreader.

In a first variant, said open channel may be of substantially constant section and is essentially coaxial with said main axis.

In a preferred variant, the distal region includes a second upstream portion essentially coaxial with the main axis and a second downstream portion having an axis extending it and terminated by said distal end, the second downstream portion having an axis that is inclined relative to said main axis, said inclination being directed more particularly away from the opening of the open channel. This disposition serves to improve the functionality of the handpiece, and more particularly it gives the practitioner a less obstructed view of the zone to be treated.

Said distal region may be implemented in the form of a distal piece suitable for being mounted on the remainder of the handpiece. This disposition makes it possible, advantageously, to use the handpiece for other types of laser surgery by fitting it to distal pieces specific to other operations.

The handpiece may then include a central piece on which the distal piece is mounted, and the central piece may include an air suction opening. The air suction opening serves to suck in the smoke given off during ablation, and consequently to clear more visibility for the practitioner, with the open channel serving as a suction guide in the distal region.

Advantageously, the handpiece may include a proximal piece including an optical device together with means for focusing or unfocusing the laser radiation, the central piece also including a gas inlet adjacent to the proximal piece in such a manner as to produce a flow of gas that protects the optical device.

In a preferred embodiment, the handpiece is connected to a source of laser radiation including means for periodically varying its optical axis, in particular in a helix, e.g. using the "Swiftlase" method of Sharplan Lasers (Allendale, N. J., USA). This suggestion is particularly advantageous in that it makes it possible to use $CO_2$ laser surgery at maximum effectiveness, with this being made possible because the handpiece has a channel with a diameter of several millimeters (in particular a diameter of 5 mm) which is completely compatible with this type of device, which makes it possible to operate with laser powers of the order of 10 watts, and which may be raised to 20 watts to 30 watts without giving rise to carbonization or bleeding.

BRIEF DESCRIPTION OF THE DRAWING

Other characteristics advantages to the invention appear more clearly on reading the following description given by way of non-limiting example and with reference to the accompanying drawing, in which:

FIG. 1 is a longitudinal section view through a first embodiment of the handpiece of the invention;

FIG. 2 is an exploded view of the component parts of the handpiece of FIG. 1; and FIG. 3 shows a preferred embodiment of the distal piece of the handpiece of the invention.

MORE DETAILED DESCRIPTION

The handpiece shown by way of example in FIGS. 1 and 2 comprises a central piece 3 having a channel region 31 with a main axis 32. A proximal piece 2 has a threaded distal end 25 screwed into the complementary proximal end 36 of the central piece 3. The proximal piece 2 includes a two-lens optical system 12 mounted in a cylindrical support 22. A cylindrical sleeve 23 suitable for being moved by the practitioner enables the optical system 21 to be moved in translation so as to focus or unfocus the laser radiation in the work region, i.e. in the vicinity of the distal end 44.

The central piece 3 includes, in a proximal region of larger section 37, firstly a suction outlet 35 connected to a tube 35' for using the channel 32 to suck out the "smoke" caused by tissue excision, and secondly a gas inlet 34 connected to a gas feed tube 34' located between the outlet 35 and the proximal region 36. It serves to inject gas at a low flow rate so as to prevent the optical system 21 being polluted by the smoke while performing a surgical operation.

The distal end 33 of the central piece 3 has a tapping enabling the threaded proximal end 41 of a distal piece 4 to be screwed thereto, with the distal piece 4 serving, in accordance with the invention, to convey the laser radiation to the treatment zone.

This endpiece 4 includes firstly a tubular region 40 defining a tubular channel 51 whose axis is the same as the axis of the channel 31 and which extends it in the distal direction, and then a region of the tubular channel which is open via a groove 52' which defines an open channel 52 extending over a length $L_5$ of about 65 mm and which has an outside diameter of about 5 mm at its distal end 44, enabling it to be inserted into the nostril of a patient.

This channel region 52 has a first portion 42 extending from the stepped distal end 55 of the region 40 to about halfway along the length $L_5$ of the open channel 52 with an external outline 46 of diameter that tapers regularly from a value of about 10 mm in the vicinity of the end 55 to the above-mentioned value of about 5 mm. This disposition makes it possible firstly to insert the end 43 easily into the nostril of a patient, since the outside shape 48 is of smaller section, whereas once fully inserted, the region 42 serves to open up the nostril of the patient and give the practitioner a field of view.

The open channel region 52 which, in the embodiment shown is opened by the groove 52' over a little less than half of its periphery performs three functions, namely:

it allows the practitioner to observe the operating region;

it serves to convey the laser radiation as provided by a $CO_2$ laser, for example, without giving rise to significant heating and thus avoids burning the nostrils of the patient; and finally it makes it possible optionally to extend the channel region 31 in such a manner as to channel gas suction via the outlet 35.

To avoid injuring the nose of the patient, the distal end 44 of the piece 4 has a rounded end 45.

In the preferred embodiment as shown in FIG. 3, the open channel region of the endpiece, now referenced 4', includes two portions, a first portion 53 situated as before in the tapering region defined by the outside shape 46 progressively tapering to about the middle of the channel region. This region defines a channel region 53 whose axis is the same as the main axis 32 of the handpiece.

The distal end $43_1$ of the piece 4' includes a channel region 54 whose axis is inclined by a few degrees (e.g. 10°), away from the opening of the open channel 54, i.e. downwards in FIG. 3. This inclination serves to improve the practitioner's view of the operative field.

As mentioned above, prior art nasal probes implementing optical fibers do not enable satisfactory operations to be performed since thy are of too small a diameter, since they can be used for a short period of time only because they wear out quickly, and also because, given their small diameter, the power conveyed can only be low given the risk of burning the internal fiber of plastics material conveying the radiation and surrounded by a metal sheath. Such nasal probes also suffer from the disadvantage of conveying focused laser radiation which, in practice, leads to a risk of secondary hemorrhage.

The handpiece of the invention, because of its endpiece 4 or 4', makes it possible to convey laser radiation at considerable power, e.g. about 10 watts to 20 watts, thereby making it possible to ablate tissue quickly from the inferior nasal conchae via the nasal cavities.

In a preferred embodiment, the handpiece uses a source of laser radiation that includes a device making it possible to vary its optical axis periodically, in particular in helical manner around the main axis 32 of the handpiece which is the same as the axis of the optical system 21, e.g. by means of the device sold under the trademark Swiftlase by Sharplan Lasers (Allendale, N. J., USA). Such "helical" laser radiation makes it possible to ablate tissue at high power (of the order of 10 watts, and possibly as much as 20 watts to 30 watts) without carbonization, thereby making larger amounts of ablation possible given that carbonization of tissue prevents the tissue underlying the carbonized tissue from being ablated.

Use of the ring 23 enables the laser radiation to be unfocused with lower risk of hemorrhage since coagulation takes place almost spontaneously.

The nasal endpiece 4 which is fixed on the piece 3 may be interchangeable, reusable, and sterilizable, thus reducing the cost of the equipment used since, in practice, it can be reused indefinitely.

The probe is made of mat black metal so as to avoid reflecting the laser radiation, and it is sufficiently fine to be inserted into the nose nearly all the way to the end of the nasal cavity, thereby enabling it to treat larger zones of tissue observed directly or possibly via a nasal endoscope.

In addition, the handpiece to which the nasal endpiece 4, 4' is fixed can be used for treating other conditions with different endpieces, e.g. in the pharynx, thus constituting another cost advantage.

By way of example, the handpiece comprises three metal parts made of blackened aluminum, the piece 2 has two focusing and unfocusing lenses and its length $L_2$ is 70 mm. The central piece 3 with smoke suction and air blowing attachments has a length $L_3$ of about 95 mm, while the endpiece 4 specific to nasal turbinectomy has a length $L_4$ of 118 mm.

An operation may be performed as described below:

A patient is placed in the sitting position, wearing protective goggles. After local anesthesia performed by spraying 15% "Lidocaine" and after installing cotton wool in the nasal cavity soaked in Lidocaine having 5% naphthazoline, a handpiece of the invention is used at a power of 20 watts to 30 watts delivered by a continuous $CO_2$ laser with helical displacement (Swiftlase method). This should enable a large amount of tissue to be ablated without carbonizing the mucous membrane of the head or of the body of the concha, in a single visit per nasal cavity, and avoiding any bone contact. The practitioner may use a blackened Killian speculum to expose the target zone better and to protect the perimeter of the nostril. After resection of the enterolateral portion of the concha, it is possible, if necessary, to use a fine metal rod to guide the laser radiation to the tail of the concha so as to complete excision of the posterolateral portion thereof. The entire operation should not last more than about 5 minutes, does not require general anesthetic, and does not require hospitalization, i.e. it can be used on outpatients.

The $CO_2$ laser should present few indirect secondary effects, and particularly little risk of ill-controlled tissue absorption.

I claim:

1. A handpiece for performing laser surgery of a nose having a nostril, said handpiece comprising a handle piece having a distal end and a proximal end, said proximal end including means for connecting said handle piece to a source of laser radiation, said handle piece having a transit region forming a channel having an axis, said transit region extending between said proximal and distal ends of the handle piece for passing laser radiation from said proximal end to said distal end of said handle piece, said handle piece including a suction outlet in communication with said transit region of said handle piece, said suction outlet including means for connecting said suction outlet to suction means, said handle piece including a distal piece having a distal end and a proximal end adapted to be mounted on said distal end of said handle piece, said distal piece having a transit region forming a channel, and having an axis coaxial with the axis of the handle piece, said transit region extending between said proximal and distal ends of said distal piece for passing laser radiation from said proximal end to said distal end of said distal piece, whereby said laser radiation travels through the transit regions of said handle piece and said distal piece to a working zone adjacent said distal end of said distal piece to perform said laser surgery, a longitudinal slit formed in said transit region of said distal piece and extending from said distal end of said distal piece, said slit defining an open channel extending over less than half of the periphery of the distal piece whereby said suction outlet enables suction to be performed in said working zone via the transit region of respectively said distal piece and said handle piece whereas said longitudinal slit allows a practitioner to observe the working zone.

2. A handpiece according to claim 1, wherein the slit formed in the distal piece has a length that is sufficient to enable said distal end of said distal piece to reach at least an inferior nasal concha of a nose to be treated, while simultaneously heaving a portion of said zone constituting said open channel outside the nose.

3. A handpiece according to claim 1, in which said distal piece tapers progressively from its proximal end toward its distal end.

4. A handpiece according to claim 1, wherein said slit defines a zone constituting said open channel, said zone being of substantially constant section.

5. A handpiece according to claim 1, wherein said transit region of the distal piece includes a proximal portion having a first axis essentially coaxial with the axis of said handle piece and said zone constituting an open channel having a second axis that is inclined relative to said first axis.

6. A handpiece according to claim 1, including a proximal piece having an optical device, said proximal piece including means for mounting said proximal piece on said proximal end of the handle piece, said optical device being adapted to receive radiation from a source of laser radiation, and said optical device having means for adjusting the focus of laser radiation.

7. A handpiece according to claim 6, and including a source of laser radiation having means for causing an optical axis of the laser radiation to vary helically on a periodic basis.

8. A handpiece for performing laser surgery of a nose having a nostril, said handpiece comprising a handle portion having a proximal end including means for connecting said handle portion to a source of laser radiation, said handle piece having a transit region forming a channel having a longitudinal axis, said transit region extending longitudinally through said handle portion for passing laser radiation therethrough, said handle portion including a suction outlet in communication with said transit region, said suction outlet including means for connecting said suction outlet to suction means, said handpiece including a distal portion having a distal end and a proximal end, the proximal end of the distal portion being coupled to said handle portion, said distal portion having a transit region forming a channel and having an axis coaxial with the axis of the proximal portion, said transit region extending longitudinally through said distal portion for passing laser radiation therethrough, whereby laser radiation may travel through the transit region of said handle portion and said distal portion to a working zone adjacent said distal end of said distal portion to perform said laser surgery, a longitudinal slit formed in said transit region of said distal portion and extending from said distal end of said distal portion, said slit defining an open channel extending over less than half of the periphery of said distal portion, whereby said suction outlet enables suction to be performed in said working zone via the transit region of respectively said distal portion and said handpiece whereas said longitudinal slit allows a practitioner to observe the working zone.

9. A handpiece according to claim 8, wherein the slit formed in the distal piece has a length that is sufficient to enable said distal end of said distal piece to reach at least an inferior nasal concha of a nose to be treated, while simultaneously heaving a portion of said zone constituting said open channel outside the nose.

10. A handpiece according to claim 8, in which said distal portion tapers progressively from its proximal end toward its distal end.

11. A handpiece according to claim 8, wherein said slit defines a zone constituting said open channel, said zone being substantially constant section.

12. A handpiece according to claim 8, wherein said transit region of the distal piece includes a proximal portion having a first axis essentially coaxial with the axis of said handle portion and said zone constituting an open channel having a second axis that is inclined relative to said first axis.

13. A handpiece according to claim 8, including a proximal piece having an optical device, said proximal piece including means for mounting said proximal piece on said proximal end of the handle piece, said optical device being adapted to receive radiation from a source of laser radiation, and said optical device having means for adjusting the focus of laser radiation.

14. A handpiece according to claim 13, and including a source of laser radiation having means for causing an optical axis of the laser radiation to vary helically on a periodic basis.

15. A handpiece for performing laser surgery of a nose having a nostril, said handpiece having a distal end and a proximal end, said proximal end including means for connecting said handpiece to a source of laser radiation, said handpiece having a transit region forming a channel having a longitudinal axis, said transit region extending from said proximal end to the distal end for passing laser radiation from said proximal end to said distal end, whereby said laser radiation travels through said transit region of said handpiece to a working zone adjacent said distal end to perform said laser surgery, said handpiece including a suction outlet in communication with said transit region of said handpiece, said transit region defining a continuous passage between said suction outlet and said distal end, said suction outlet including means for connecting said suction outlet to suction means, a longitudinal slit formed in said handpiece and extending from said distal end, said slit terminating between said distal end and said suction outlet, said slit defining an open channel extending over less than half of the periphery of said handpiece at said distal end, whereby said suction outlet enables suction to be performed in said working zone via the transit region of said handpiece while said longitudinal slit allows the practitioner to observe said working zone.

* * * * *